(12) United States Patent
Borg-Capra et al.

(10) Patent No.: US 6,861,233 B1
(45) Date of Patent: Mar. 1, 2005

(54) METHOD OF SCREENING FOR TRIACYGLYCEROL HYDROLASE INHIBITORS

(75) Inventors: Catherine Sylvia Borg-Capra, Les Ulis (FR); Richard Jiri Lehner, Edmonton (CA); Dennis Edward Vance, Edmonton (CA)

(73) Assignees: Glaxo Group Limited (GB); The Governors of the University of Alberta (CA)

( * ) Notice: Subject to any disclaimer, the term of this patent is extended or adjusted under 35 U.S.C. 154(b) by 388 days.

(21) Appl. No.: 10/049,113

(22) PCT Filed: Aug. 24, 2000

(86) PCT No.: PCT/EP00/08262

§ 371 (c)(1),
(2), (4) Date: Feb. 8, 2002

(87) PCT Pub. No.: WO01/16358

PCT Pub. Date: Mar. 8, 2001

(30) Foreign Application Priority Data

Aug. 28, 1999 (GB) .............................. 9920334

(51) Int. Cl.[7] .............................. C12Q 1/60
(52) U.S. Cl. ........................ 435/11; 435/375
(58) Field of Search ........................ 435/11, 18, 69.2, 435/375

(56) References Cited

U.S. PATENT DOCUMENTS 5,356,787 A  * 10/1994 Gross .......................... 435/18

FOREIGN PATENT DOCUMENTS

| FR | 2767136 | 2/1999 |
|---|---|---|
| WO | WO 98/24888 | 6/1998 |

OTHER PUBLICATIONS

Lehner R. Purification and Characterization of a Porcine Liver Microsomal Triacylglycerol Hydrolase. Biochemistry 1997, vol. 36, pp. 1861–1868.*
Lehner R. Subcellular Localization, Development Expression and Characterization of a Liver Triacylglyerol Hydrolase. Biochemistry J Mar. 1999, vol. 338, pp. 761–768.*
Bitou et al., "Screening of lipase inhibitors from marine algae," *Lipids* 34:5 441–445 (May 1999).
Hashida et al., "Phase–Transfer–Catalyzed Azo Coupling Reactions in Two–Phase Systems," *Bulletin of the Chemical Society of Japan* 61:905–910 (1988).
Juhel et al., "Green tea extract (AR25(R)) inhibits lipolysis of triglycerides in gastric and duodenal medium in vitro," *Journal of Nutritional Biochemistry* 11:1 45–51 (Jan. 2000).
Knunyants et al., "Transformations of alpha,alpha–Difluorocarbonyl Compounds 4. Reaction of Polyfluoro Ketones with Phenylhydrazine," *Bulletin of the Academy of Sciences of the USSR. Division of Chemical Science* 29:8 1336–1341 (Jun. 1980).

Krishnankutty et al., "Metal Chelates of Phenylhydrazonothenoyltrifluoroacetone," *Journal of the Indian Chemical Society* 70:3 238–239 (1993).
Lehner et al., "Purification and characterization of a porcine liver microsomal triacylglycerol hydrolase," *Biochemistry* 36:7 1861–1868 (1997).
Lehner et al. "Subcellullar localization, developmental expression and characterization of a liver triacylglycerol hydrolase," *Biochemical Journal* 338:3 761–768 (Mar. 1999).
Lehner et al., "Cloning and expression of a cDNA encoding a hepatic microsomal lipase that mobilizes stored triacylgycerol," *Biochemical Journal* 343:1 1–10 (Oct. 1999).
Mitchell et al., "Spectroscopic Studies of Tautomeric Systems—III. 2–Arylhydrazones of 1,2,3–Triketones," *Tetrahedron* 35:2013–2019 (1979).
Wiggins et al., "The Lipolysis–Esterification Cycle of Hepatic Triacylglycerol Its role in the Secretion of Very–Low–Density Lipoprotein and Its Response to Hormones and Sulphonylureas," *Biochemical Jounral* 284:2 457–462 (1992).
Francone O.L., et al., "Contribution of cytoplasmic storage triacylglycerol to VLDL–triacygylcerol in isolated rat hepatocytes." Biochimica et Biophysica Acta. 1989; 1002:28–36.
Wiggins D., et al. "The lipolysis/esterification cycle of hepatic triacyglycerol. Its role in the secretion of very–low–density lipoprotein and its response to hormones and sulphonylureas." Biochemical Journal. 1992; 284:457–462.
Buchwald H., et al. "Effect of partial ilial bypass on mortality and morbidity from coronary artery disease in patients with hypercholesterolemia–Report of the Progam on Surgical Control of the Hyperlipidemia (POSCH)." New England Journal of Medicine. 1990; 323:946.
Becker A., et al. Purification, cloning, and purification of a human enzyme with acyl coenzymz A:cholestero acyltransferase activity, which is identical to liver carboxylesterase. Arterioscler. Thromb. 1994; 14:1346–1355.
Gibbons, G.F., et al. "Intracellular triacylglycerol lipase: its role in the assembly of hepatic very–low–density lipoprotein (VLDL)." Advances in Enzyme Regulation. 1995; 35:179–198.

(List continued on next page.)

*Primary Examiner*—Ralph Gitomer
(74) *Attorney, Agent, or Firm*—Virginia G. Campen

(57) ABSTRACT

The invention relates to methods of identifying therapeutic agents which inhibit triacyglycerol hydrolase (TGH) activity, defined as TGH inhibitors, which are useful in the treatment of conditions resulting from elevated circulating levels of TG, VLDL/LDL-cholesterol and ApoB-100. Also claimed are therapeutic agents which are TGII inhibitors, identifiable by such methods and their use in combating diseases associated with elevated circulating levels of TG, VLDL/LDL-cholesterol and ApoB-100.

3 Claims, 3 Drawing Sheets

OTHER PUBLICATIONS

Yang L.Y., et al. "Contribution of de novo fatty acid synthesis to very low density lipoprotein triacylglycerols: evidence from mass isotopmer distribution analysis of fatty acids synthesized from [2H6]ethanol." Journal of Lipid Research. 1996; 37:262–274.

Lehner R., et al. "Purification and characterization of a porcine liver microsomal triacylglycerol hydrolase." Biochemistry. 1997; 36:1861–1868.

Lehner R., et al., "Subcellullar localization, development expression and characterization of a liver triacyglycerol hydrolase." Biochemical Journal. 1999;338:761–768.

Lehner R., et al. "Cloning and expression of a cDNA encoding a hepatic microsomal lipase that mobilizes stored triacylglycerol." Biochemical Journal. (Oct.) 1999;343:1–10R.

* cited by examiner

FIG. 1

Sequence of the human TGH

MWLRAFILATLSASAAWG-HPSSPPVVDTVHGKVLGKFVSLEGFAQPVAIFLGIPFGKPP

LGPLRFTPPQPAEPWSFVKNATSYPPMCTQDPKAGQLLSELFTNRKENIPLKLSEDCLYL

NIYTPADLTKKNRLPVMVWIHGGGLMVGAASTYDGLALAAHENVVVVTIQYRLGIWGFFS

TGDEHSRGNWGHLDQVAALRWVQDNIASFGGNPGSVTIFGESAGGESVSVLVLSPLAKNL

FHRAISESGVALTSVLVKKGDVKPLAEQIAITAGCKTTTSAVMVHCLRQKTEEELLETTL

KMKFLSLDLQGDPRESQPLLGTVIDGMLLLKTPEELQAERNFHTVPYMVGINKQEFGWLI

PMLMSYPLSEGQLDQKTAMSLLWKSYPLVCIAKELIPEATEKYLGGTDDTVKKKDLFLDL

IADVMFGVPSVIVARNHRDAGAPTYMYEFQYRPSFSSDMKPKTVIGDHGDELFSVFGAPF

LKEGASEEEIRLSKMVMKFWANFARNGNPNGEGLPHWPEYNQKEGYLQIGANTQAGQKLK

DKEVAFWTNLFAKKAVEKPPQTEHIEL

FIG. 2

| | Edman N-terminal sequence | Mass spectre |
|---|---|---|
| Purified Human TGH | SSPPVVDTVHGKVLGKFVSLEGFAQPVA | 62kDa |
| Pig TGH | ASPPVVDTAQGRVLGKYVSLEGLAQPVA | 60kDa |
| Cloned Human TGH | SSPPVVDTVHGKVLGKFVSLEGFAQPVA | |

SEQUENCE LISTING

<160> NUMBER OF SEQ ID NOS: 7

<210> SEQ ID NO 1
<211> LENGTH: 566
<212> TYPE: PRT
<213> ORGANISM: Homo sapiens

<400> SEQUENCE: 1

Met Trp Leu Arg Ala Phe Ile Leu Ala Thr Leu Ser Ala Ser Ala Ala
 1               5                  10                  15

-continued

```
Trp Gly His Pro Ser Ser Pro Val Val Asp Thr Val His Gly Lys
         20                  25                  30

Val Leu Gly Lys Phe Val Ser Leu Glu Gly Phe Ala Gln Pro Val Ala
     35                  40                  45

Ile Phe Leu Gly Ile Pro Phe Gly Lys Pro Pro Leu Gly Pro Leu Arg
     50                  55                  60

Phe Thr Pro Pro Gln Pro Ala Glu Pro Trp Ser Phe Val Lys Asn Ala
 65                  70                  75                  80

Thr Ser Tyr Pro Pro Met Cys Thr Gln Asp Pro Lys Ala Gly Gln Leu
             85                  90                  95

Leu Ser Glu Leu Phe Thr Asn Arg Lys Glu Asn Ile Pro Leu Lys Leu
            100                 105                 110

Ser Glu Asp Cys Leu Tyr Leu Asn Ile Tyr Thr Pro Ala Asp Leu Thr
            115                 120                 125

Lys Lys Asn Arg Leu Pro Val Met Val Trp Ile His Gly Gly Gly Leu
130                 135                 140

Met Val Gly Ala Ala Ser Thr Tyr Asp Gly Leu Ala Leu Ala Ala His
145                 150                 155                 160

Glu Asn Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu Arg Trp Val Gln Asp Asn Ile Ala Ser Phe
            195                 200                 205

Gly Gly Asn Pro Gly Ser Val Thr Ile Phe Gly Glu Ser Ala Gly Gly
        210                 215                 220

Glu Ser Val Ser Val Leu Val Leu Ser Pro Leu Ala Lys Asn Leu Phe
225                 230                 235                 240

His Arg Ala Ile Ser Glu Ser Gly Val Ala Leu Thr Ser Val Leu Val
            245                 250                 255

Lys Lys Gly Asp Val Lys Pro Leu Ala Glu Gln Ile Ala Ile Thr Ala
            260                 265                 270

Gly Cys Lys Thr Thr Thr Ser Ala Val Met Val His Cys Leu Arg Gln
        275                 280                 285

Lys Thr Glu Glu Glu Leu Leu Glu Thr Thr Leu Lys Met Lys Phe Leu
    290                 295                 300

Ser Leu Asp Leu Gln Gly Asp Pro Arg Glu Ser Gln Pro Leu Leu Gly
305                 310                 315                 320

Thr Val Ile Asp Gly Met Leu Leu Lys Thr Pro Glu Glu Leu Gln
            325                 330                 335

Ala Glu Arg Asn Phe His Thr Val Pro Tyr Met Val Gly Ile Asn Lys
            340                 345                 350

Gln Glu Phe Gly Trp Leu Ile Pro Met Leu Met Ser Tyr Pro Leu Ser
        355                 360                 365

Glu Gly Gln Leu Asp Gln Lys Thr Ala Met Ser Leu Leu Trp Lys Ser
    370                 375                 380

Tyr Pro Leu Val Cys Ile Ala Lys Glu Leu Ile Pro Glu Ala Thr Glu
385                 390                 395                 400

Lys Tyr Leu Gly Gly Thr Asp Thr Val Lys Lys Lys Asp Leu Phe
            405                 410                 415

Leu Asp Leu Ile Ala Asp Val Met Phe Gly Val Pro Ser Val Ile Val
            420                 425                 430
```

-continued

```
Ala Arg Asn His Arg Asp Ala Gly Ala Pro Thr Tyr Met Tyr Glu Phe
        435                 440                 445

Gln Tyr Arg Pro Ser Phe Ser Ser Asp Met Lys Pro Lys Thr Val Ile
    450                 455                 460

Gly Asp His Gly Asp Glu Leu Phe Ser Val Phe Gly Ala Pro Phe Leu
465                 470                 475                 480

Lys Glu Gly Ala Ser Glu Glu Ile Arg Leu Ser Lys Met Val Met
                485                 490                 495

Lys Phe Trp Ala Asn Phe Ala Arg Asn Gly Asn Pro Asn Gly Glu Gly
            500                 505                 510

Leu Pro His Trp Pro Glu Tyr Asn Gln Lys Glu Gly Tyr Leu Gln Ile
        515                 520                 525

Gly Ala Asn Thr Gln Ala Gly Gln Lys Leu Lys Asp Lys Glu Val Ala
    530                 535                 540

Phe Trp Thr Asn Leu Phe Ala Lys Lys Ala Val Glu Lys Pro Pro Gln
545                 550                 555                 560

Thr Glu His Ile Glu Leu
                565
```

<210> SEQ ID NO 2
<211> LENGTH: 28
<212> TYPE: PRT
<213> ORGANISM: Homo sapiens

<400> SEQUENCE: 2

```
Ser Ser Pro Pro Val Val Asp Thr Val His Gly Lys Val Leu Gly Lys
  1               5                  10                  15

Phe Val Ser Leu Glu Gly Phe Ala Gln Pro Val Ala
            20                  25
```

<210> SEQ ID NO 3
<211> LENGTH: 28
<212> TYPE: PRT
<213> ORGANISM: Sus scrofa

<400> SEQUENCE: 3

```
Ala Ser Pro Pro Val Val Asp Thr Ala Gln Gly Arg Val Leu Gly Lys
  1               5                  10                  15

Tyr Val Ser Leu Glu Gly Leu Ala Gln Pro Val Ala
            20                  25
```

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: conserved
      sequence found in mouse, rat, and pig triacylglycerol hydrolase
      (TGH) cDNA

<400> SEQUENCE: 4
gcatctgggg attcttcagc acagggatg aacacagccg                    40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: conserved
      sequence found in mouse, rat, and pig triacylglycerol hydrolase
      (TGH) cDNA -continued

```
<400> SEQUENCE: 5
gagcaaagtt ggcccagtat ttcatcacca ttttgctgag                    40

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: 5' end of
      human carboxylesterase-1 (hCE1)

<400> SEQUENCE: 6
aactgtcgcc cttcacgatg tg                                       22

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: 3' end of
      human carboxylesterase-1 (hCE1)

<400> SEQUENCE: 7
tcacagctct atgtgttctg tctgg                                    25
```

METHOD OF SCREENING FOR TRIACYGLYCEROL HYDROLASE INHIBITORS

The present invention relates to the use of triacyglycerol hydrolase (TGH), it's use in methods of screening for agents which inhibit TGH, and to agents having TGH inhibition characteristics for use in combating diseases associated with elevated lipid levels.

There is convincing evidence that hyperlipidemia is a major risk factor for coronary heart disease (CHD) [1–2]. Several studies of lipid-lowering drugs have demonstrated a reduction in coronary endpoints accompanied with a beneficial effect on the progression of atherosclerosis [3–51.

Lipids are transported in the blood plasma and from different tissues in the body in the form of lipoproteins. Very-low-density lipoprotein (VLDL) is the principal vehicle for the transport of endogenous triglycerides (TG), and, ultimately, through its metabolic product, low-density lipoprotein (LDL), of cholesterol as well. VLDL is synthesized in the liver. Although many dyslipidaemia are characterized by excessive rate of production and secretion of hepatic VLDL [6–7], little is known of the molecular mechanisms involved in the origin and transfer of lipid, particularly TG to the developing VLDL particle. However, it seems likely that TG synthesized de novo in the endoplasmic reticulum from fatty acids are not immediately transferred to nascent VLDL [8]. Instead TG, that are destined for incorporation into VLDL are stored temporarily within the cell cytosol [9]. In vitro and in vivo evidence supports the concept that this storage pool is the source of much of the TG which appear in VLDL (70%) [9–11]. TG from storage droplets are mobilized by lipolysis, and the fatty acid re-esterified before incorporation in the VLDL [11–12]. The rate at which this process operates may determine the effective availability of TG at the site of VLDL assembly and therefore may represent an important regulatory step for VLDL secretion. The nature of the lipases involved in the cycle of lipolysis/reesterification is currently unknown as is their exact location within the cell. A candidate lipolytic enzyme, lysosomal acid lipase was considered. However, since chloroquine did not affect the bulk of intracellular hydrolysis of TG, it appeared that other lipases might be involved in the mobilization of TG for VLDL synthesis and secretion [12]. Also, the lipolysis/re-esterification cycle was resistant to insulin, suggesting that it is not a hormone-sensitive lipase similar to that, which occurs in adipose tissue [12].

A microsomal TG hydrolase purified from porcine liver has been described [13]. The enzyme is located in the endoplasmic reticulum and mitochondria-associated membranes, organelles where de novo TG synthesis and assembly take place. The triacylglycerol hydrolase (TGH) has been shown to be associated with lipid droplets. TGH is expressed in rat liver toward the end of the suckling period that coincides with the ontology of lipoprotein secretion. TGH is present exclusively to liver cells surrounding the capillary vessels, an area that it is likely to be active in lipoprotein production and secretion. In addition, the enzyme is absent from liver-derived HepG2 and McArdleRH7777 hepatoma cells which are known to have impaired VLDL assembly and secretion 114]. Taking these results together, it has been suggested that TGH may participate in the mobilization of TG for assembly into VLDL.

It has now been found by the inventors that TGH modulates circulating TG levels in a mammalian subject, which provides the use of TGH as a target for screening for the identification of compounds for the treatment of diseases which are ameliorated by lowering TG levels, such as pancreatitis. The inventors have additionally found that TGH modulates circulating VLDL/LDL-cholesterol and apolipoprotein B-100 (ApoB-100) levels in a mammalian subject. Thus, TGH is also a target for screening for the identification of compounds useful in the treatment of diseases which are ameliorated by lowering VLDL/LDL-cholesterol and ApoB-100 levels, such as mixed dislipidemia.

The cDNA encoding the rat hepatic TGH has been cloned and expressed [15].

McArdle RH7777 rat hepatoma cell lines stably expressing the rat liver TGH displayed a higher utilization of intracellular triacylglycerol pools for secretion, and a higher secretion of ApoB-100 in the medium than the non transfected cell lines. These results strengthen the finding of the active role of TGH in the mobilization of stored TG, which can be used for lipoprotein assembly.

Thus, according to a first aspect, the present invention provides a method for identifying compounds which will be useful in the treatment of conditions resulting from elevated circulating levels of:
i) TG;
ii) TG, VLDL/LDL-cholesterol and ApoB-100; or
iii) VLDL/LDL-cholesterol and ApoB-100; comprising the step of determining whether the compound inhibits TGH activity.

As a preferred aspect, the treatment is of conditions resulting from elevated circulating levels of VLDL/LDL-cholesterol and ApoB-100.

As a further preferred aspect, the method comprises detecting or assaying the extent or result of enzymatic activity or lipolysis of TGH on a control substrate, in the presence of and absence of said TGH inhibitor.

Methods of detection of enzyme activity according to the present invention comprise any suitable methods known in the art. Thus, a control substrate, as defined herein, may comprise a labelled compound, (i.e. one which is radioactive or fluorescent) and/or one which is photo-activable. An example of a suitable control substrate is 4-methylumbelliferyl butyrate.

The present invention demonstrates that an agent which inhibits TGH enzymatic activity (lipolysis) decreases to an equally strong extent the circulating levels of TG, VLDL/LDL-cholesterol and apolipoprotein B-100 in a mammalian subject.

The effect of TGH inhibition on TG is by no means certain from the teaching of the prior art. In fact, TGH is only one of a number of lipases which may have been involved in the process, and there is no teaching that inhibition of TGH alone would exhibit a sufficient therapeutic effect. The further observation of the effect of TGH inhibition on VLDL/LDL-cholesterol and apolipoprotein B-100 is surprising in that this effect is not linked to the role of TGH in decreasing circulating TG. Thus, the additional finding represents a further effective method of treating specific diseases associated with elevated lipid levels, which is neither taught nor suggested by the prior art.

As used herein, the 'methods for identification' include any screen or assay whereby the action of an agent capable of modulating, affecting, influencing or interfering with the enzymatic activity of TGH is investigated, and includes inhibition assays in which a single agent or compound is investigated as well as assays in which more than one compound, such as an array of compounds, or a library of compounds is tested. In the case of testing more than one agent, these tests may be either simultaneous or sequential. The methods of detection and assay include any quantitative, qualitative or semiquantitative assessment of whether there is any inhibition of enzymatic activity of TGH on a substrate in the presence of the agent being tested, compared with that in the absence of said agent.

In one aspect, the method of the invention comprises an inhibition assay whereby the difference in enzymatic activity of TGH on a fluorogenic control substrate in the presence of a test TGH inhibitor, with that in the absence of said test inhibitor is compared.

In another aspect, the present invention comprises a functional in vivo assay whereby the extent of hypolipidemic activity is determined when the test TGH inhibitor is administered to a test mammalian subject, for example, a hamster.

Viewed from a further aspect, the present invention provides a therapeutic agent (a 'TGH inhibitor'), identified or identifiable by the aforementioned methods according to the present invention, and its use in combating diseases associated with elevated circulating levels of lipids.

In a further alternative or yet further aspect, there is provided a method for the treatment of conditions resulting from elevated circulating levels of:
i) TG;
ii) TG, VLDL/LDL-cholesterol and ApoB100; or
iii) VLDL/LDL-cholesterol and ApoB-100; comprising administration of a compound identified by the aforementioned method for identification of suitable compounds.

The invention provides, as a further aspect, the use of a compound which inhibits the action of TGH, or a physiologically acceptable salt, solvate or derivative thereof, in the preparation of a medicament for the treatment of conditions resulting from elevated circulating levels of:
i) TG;
ii) TG, VLDL/LDL-cholesterol and ApoB-100; or
iii) VLDL/LDL-cholesterol and ApoB-100.

The use, above, in the preparation of a medicament of conditions resulting from elevated circulating levels of VLDL/LDL-cholesterol and ApoB-100 is preferred.

In an alternative or further aspect, there is provided a method for the treatment of a mammal, including man, in particular in the treatment of conditions resulting from elevated circulating levels of:
i) TG;
ii) TG, VLDL/LDL-cholesterol and ApoB-100; or
iii) VLDL/LDL-cholesterol and ApoB-100; comprising administration of an effective amount of a compound which inhibits the action of TGH, or a physiologically acceptable salt, solvate or derivative thereof.

Compounds of the invention which inhibit TGH activity are of use in the treatment of disease associated with elevated lipid levels. Diseases which result from elevated levels of circulating TG (i.e. hypertriglyceridemia, hyperbetalipoproteinemia) include pancreatitis and obesity. Diseases in which elevated levels of TG, VLDL/LDL-cholesterol and ApoB-100 are implicated (i.e. mixed dyslipidemia, hypercholesterolemia, hyperbetalipoproteinemia) include non-insulin dependent diabetes mellitus (NIDDM), coronary arterial disease, peripheral vascular disease and cerebra-vascular disease. Diseases in which elevated levels of VLDL/LDL-cholesterol and ApoB-100 are implicated (i.e. hypercholesterolemia, hyperbetalipoproteinemia) include non-insulin dependent diabetes mellitus (NIDDM), coronary arterial disease, peripheral vascular disease and cerebro-vascular disease.

Further, TGH is involved in the cycle of lipolysis-esterification of TG, early steps in the assembly of TG in VLDL. TGH is also present in the intestine [13] and is expected to have similar function. Therefore, TGH in the intestine might participate in the assembly of TG into chylomicrons and as a consequence modulate lipid absorption. Inhibition of TGH specifically in the intestine or in concert with hepatic TGH inhibition by compounds of the further aspects of the present invention may decrease the absorption of dietary lipid. Yet further, it is well recognized that lipids and associated lipoproteins and apolipoproteins play a significant role in the formation and progression of atherosclerosis disease. Numerous angiographic trials have shown that reducing cholesterol levels in patients with coronary heart disease can significantly slow progression and in some cases actually cause regression, of atherosclerosis in these patients [5, 16]. Therefore, TGH inhibitors of the further aspects of the present invention, by reducing TG, VLDL/LDL-cholesterol and Apo-B100, may represent an effective treatment of atherosclerosis.

It will be appreciated that reference to treatment is intended to include prophylaxis in patients deemed to be at risk of suffering a clinical event as a result of elevated lipids levels (primary prevention), also in patients deemed to be at risk of suffering a second or further clinical event as a result of elevated lipids levels (secondary prevention), as well as the alleviation of established symptoms. TGH inhibitors according to the invention may be administered as the raw chemical but the active ingredient is preferably presented as a pharmaceutical formulation.

Accordingly, the invention also provides a pharmaceutical composition which comprises at least one TGH inhibitor, or a physiologically acceptable salt, solvate or derivative thereof, together with one or more pharmaceutically acceptable derivatives and formulated for administration by any convenient route.

Such compositions are preferably in a form adapted for use in medicine, in particular human medicine, and can conveniently be formulated in a conventional manner using one or more pharmaceutically acceptable carriers or excipients.

Thus, TGH inhibitors according to the present invention may be formulated for oral, buccal, parenteral, transdermal, topical (including ophthalmic and nasal), depot or rectal administration or in a form suitable for administration by inhalation or insufflation (either through the mouth or nose), by methods well known in the art.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

For transdermal administration the compounds according to the invention may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

The compounds of the invention may be formulated for parenteral administration by bolus injection or continuous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unit dose device or alternatively as a powder mix with a suitable carrier for administration using a suitable delivery device.

The compositions may contain from 0.1% upwards, e.g. 0.1–99% of the active material, depending on the method of administration. A proposed dose of the compounds of the invention is 0.25 mg/kg to about 125 mg/kg bodyweight per day e.g. 20 mg/kg to 0.100 mg/kg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

TGH inhibitors according to the invention may, if desired, be administered with one or more therapeutic agents and formulated for administration by any convenient route in a conventional manner. Appropriate doses will be readily appreciated by those skilled in the art. For example, TGH inhibitors according to the invention may be administered in combination with other lipid lowering drugs acting through cholesterol depletion or by reducing VLDL production, for instance inhibition of enzymes involved in cholesterol biosynthesis such as an HMGCo-A reductase inhibitor, or a microsomal triglyceride transfer protein (MTP) inhibitor and/or a bile acid sequestrant or bile acid transporter inhibitor.

The invention will now be described with reference to the following non-limiting examples in which:

FIG. 1 shows the deduced amino acid sequence of the Human TGH from the cDNA sequence FIG. 2 shows a comparison between the N-terminal residues of purified human TGH, porcine TGH and cloned human TGH;

BIOLOGICAL EXPERIMENTAL METHODS

Materials

Figure 3:
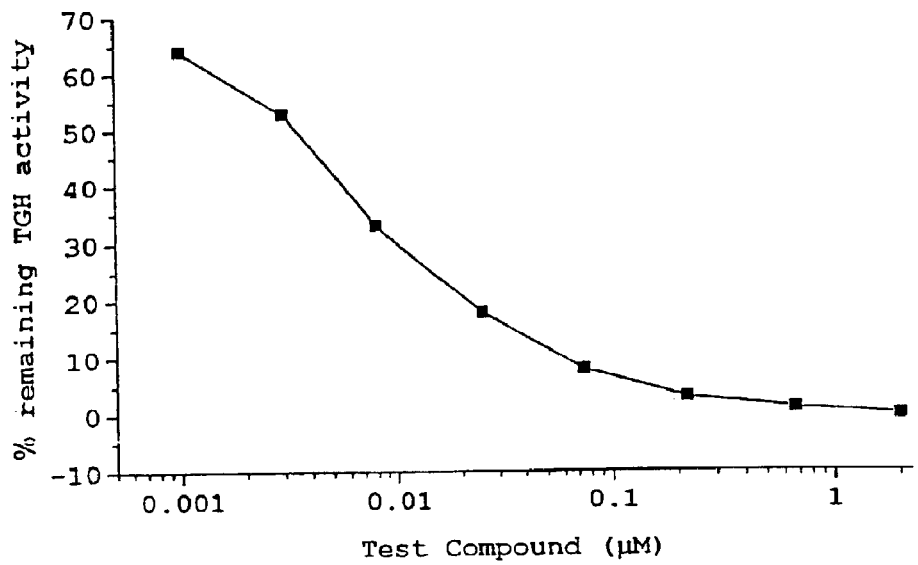
FIG. 3 shows the dose-dependent inhibition of TGH enzymatic activity with a test TGH inhibitor.

Test TGH inhibitor, 4,4,4-trifluoro-2–12-(3-methylphenyl)hydrazono]-112-thienyl)butane-1,3-dione was obtained from Maybridge. The high 0 arud Hydroxyapatite cartridges were from Bio-Rad S. A. [9,10-$^3$H(N) Trioleoylglycerol was purchased from Dupont-NEN. Enzymatic assay kits for cholesterol and triglycerides were obtained from Bio Merieux. The polyclonal antibody against the porcine TGH was provided by Dr Lehner and Dr Vance from the University of Alberta, Edmonton. All other reagents including the fluorogenic substrate 4-methylumbelliferyl butyrate and lipoprotein lipase were purchased from Sigma.

1. Cloning of the Human TGH

Two 40 nucleotides long oligos, P-TGHI (5'GCATCTGGGGATTCTTCAGCACAGGGGATGAACA CAGCCG3') and P-TGHII (5'GAGCAAAGTTGGCCC AGTATTTCATCACCATTTTGCTGAG3'), corresponding to highly conserved sites between mouse, rat and pig TGH cDNAs (15), were used to amplify a 1 kb fragment using PCR (in 50 ml 1×PCR buffer: 1 mg human liver lgt11 cDNA library, 0.4 mM of each primer, 0.25 mM dNTPs, 2 mM MgCl$_2$, 2.5U Tag polymerase; 5 min hot-start 9° D. C, 1 min 95° C., 1 min 52° C., 1 min 72° C. 30 cycles, 5 min 72° C.). This fragment was sequenced and compared to existing data base using BLAST search. It was identified as human carboxylesterase I (hCEI).

hTGH protein was purified from human liver. Upon amino acid sequencing of the first 20 residues, it was found to be the same as hCEI's first 20 amino acids.

From these 2 lines of evidence, it is confirmed that hTGH is the same as hCEI.

Two 22 nucleotides long oligos,
hCE5'For(5'AACTGTCGCCCTTCACGATGTG3') and hCE3'Rev (5'TCACAGCTCTATGTGTTCTGTCTGG3'), corresponding to the 5' and 3' of hCEI respectively, were used to amplify the 1.7 kb complete cDNA using PCR (in 50 ml 1×PCR buffer: 1 mg phage cDNA library, 0.4 mM of each primer, 0.25 mM dNTPs, 2 mM $MgCl_2$, 2.5U Taq polymerase; 5 min hot-start 95° C., 1 min 95° C., 1 min 54° C., 1 min 72° C., 40 cycles, 5 min 72° C.). The cDNA was ligated to pCR2.1TOPO (Invitrogen) to obtain cloning sites, sequenced to ensure fidelity, before finally cloned into mammalian expression vector pCI (Promega) between Xho I and Xba I.

2. Purification of Human Liver TGH

Human liver TGH was purified according to Lehner and Verger's protocol described for the porcine liver TGH [13]. Briefly, the enzyme from microsomal membranes of liver tissues was solubilised by the zwitterionic detergent 3-[(3 cholamidopropyl)dimethylammonio]-1-propanesulfonate (CHAPS) and was purified to apparent homogeneity by sequential chromatography on Q-sepharose and hydroxyapatite.

3. Effect of test agents on human liver TGH.

The enzymatic activity of TGH was evaluated with the fluorogenic substrate 4-methylumbelliferyl butyrate (4-MU-butyrate). Briefly, 10 $\mu$l of a solution of 25 mM of 4-MU-butyrate in tetrahydrofuran was injected in 2 ml of a buffer containing Tris (20 mM), pH 8.0, EDTA (1 mM) and taurodeoxycholate (300 $\mu$M). TGH activity was assayed at 1.16 nM in a final volume of 100 $\mu$l. The compound was dissolved in DMSO to be tested at various concentrations (from 1 nM to 2 $\mu$M) and was incubated with the enzyme 15-min prior to the addition of 20 $\mu$l of the substrate, which gives the starting point of the enzymatic reaction. The reaction mixture comprised of 60 $\mu$l of buffer (Tris 20 mM, pH 8, EDTA 1 mM), 10 $\mu$l of the compound at various dilutions or 10 $\mu$l of corresponding DMSO concentrations (for the 100% TGH activity), 10 $\mu$l of TGH and 20 $\mu$l of substrate.

The basal level of fluorescence of the substrate was evaluated in a reaction mixture of 70 $\mu$l of buffer, 10 $\mu$l of DMSO (at the appropriate dilution) and 20 $\mu$l of substrate, and was subtracted from each other data. Rates of lipolysis were determined from continuous increase in fluorescence intensity at 460 nm (Excitation: 355 nm).

4. Effect of TGH Inhibitors on the Lipoprotein Lipase Activity:

In order to evaluate the specificity of TGH inhibitors toward TGH, test compound was tested on the enzymatic activity of lipoprotein lipase (LPL) from bovine milk. For this purpose radiolabelled trioleoylglycerol (250 $\mu$M, specific activity 1 mCi/mmole) was emulsified in mixture of 10% gum arabic by sonication. Long-chain triacylglycerol hydrolysis was assayed in a final volume of 200 $\mu$l containing LPL (1.5 $\mu$g/ml), Tris (50 mM), pH 8.0; $MgCl_2$ $CaCl_2$ (1 mM), and 150 mM NaCl with 1 mg/ml BSA as a fatty acid acceptor for 30 min at 37° C. The reaction was terminated with the addition of 3.25 ml of methanol/chloroform/heptane (3.85:3.42:2.73 by volume); 0.3 ml of 150 mM NaCl, lipid carriers (100 $\mu$g of unlabelled oleic acid), and 50 $\mu$l of 1 N NaOH. The mixture was vortexed and centrifuged. One ml of the upper phase (containing the fatty acids that have been hydrolyzed) was mixed with 10 ml of Cytoscint and counted. Test compound is incubated with the enzyme 15 minutes prior to the addition of the substrate.

5. Hypolipidemic Activity of the TGH Inhibitor in Hamster

Ten normal fed hamsters were randomly allocated into 2 groups. Animals from one group were orally gavaged with a test TGH inhibitor in DMSOI Labrafil (10/90%), 25 mg/kg, twice a day for 3 days while the animals from the other group were gavaged with the solvent (DMSOI/abrafil) twice a day for 3 days. The animals were sacrificed 4 hours following the last administration and the plasma lipids and lipoproteins were analyzed.

Total cholesterol (TC) and triglyceride (TG) levels in plasma were determined enzymatically with reagents from Bio Merieux. VLDL/LDL lipoprotein fractions were separated from the HDL lipoproteins by gradient centrifugation (d=1.063). Cholesterol in the VLDL/LDL as well as in the HDL fraction was also determined using the Bio Merieux kit. Apolipoprotein B-100 (Apo-B100) in the VLDL/LDL fraction was visualized by using SDS-PAGE under reducing conditions using resolving gels containing a 5% to 12% gradient.

Biological Results

1. Cloning of the Human TGH

The Human TGH cDNA was isolated by PCR using specific primers designed on the rat TGH cDNA [15] and human liver cDNA library as a template. As illustrated in FIG. 1, the cDNA encodes a human carboxylesterase previously identified as human carboxylesterase EST-1 (Accession number P23141). Since the identification of human TGH as the human carboxylesterase, a paper was uncovered that mentioned the purification and cloning of a human enzyme with Acyl coenzyme A:cholesterol acyltransferase activity identical to the human carboxylesterase EST-1 [17]. The putative dual function in TG hydrolysis and cholesterol esterification is relevant to the function of TGH in the liver and intestine. Indeed it implies that the enzyme impairs the assembly of the VLDL particles by acting at both levels: lipolysis and re-esterification 2. Purification of Human Liver TGH The purified protein migrated in SDS-polyacrylamide gel electrophoresis as a single band of an apparent molecular weight of 62 kDa which is comparable to the porcine TGH (60 kDa). As shown by FIG. 2, the amino acid sequence of 28 N-terminal residues shared a high degree of homology with the porcine TGH and was identical to the human TGH. Finally, the polyclonal antibody raised against the porcine TGH which has been shown to be specific to the enzyme [13] cross-reacted with the purified human protein as well as the rat TGH [13]. These data present strong evidence that the purified protein is the human TGH.

3. Effect of test agents on human liver TGH

As shown by FIG. 3, pre-incubation of human liver TGH with test inhibitor, 4,4,4-trifluoro-2-[2-(3-methylphenyl) hydrazono]-1-(2-thienyl)butane-1,3-dione, resulted in a dose-dependent inhibition of the enzymatic activity. The concentration of 4,4,4-trifluoro-2-[2-(3-methylphenyl) hydrazono]-1-(2-thienyl)butane-1,3-dione which resulted in 50% inhibition of TGH was evaluated to be 4 nM.

Figure 4:
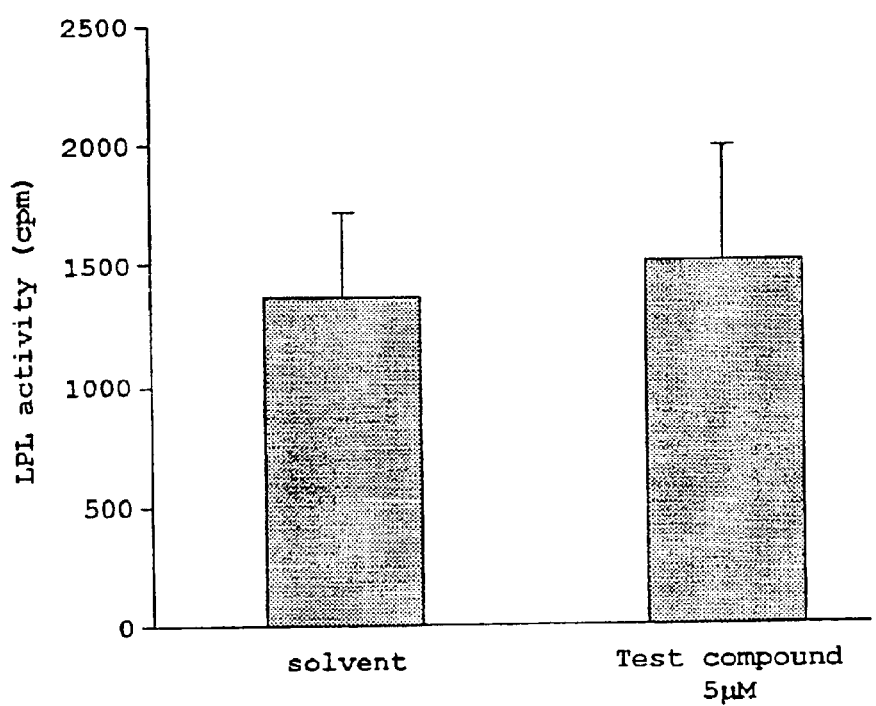
FIG. 4 shows the enzymatic activity of LPL in the presence of and absence of test TGH inhibitor.

4. Effect of TGH Inhibitors on the Lipoprotein Lipase Activity:

4,4,4-Trifluoro-2-[2-(3-methylphenyl)hydrazono-1-(2-thienyl)butane-1,3-dione was tested at 5 $\mu$M and was incubated with the enzyme 15-min prior to the addition of the substrate. As shown by FIG. 4, 4,4,4-trifluoro-2-[2-(3-methylphenyl)hydrazono]-1-(2-thienyl)butane-1,3-dione at 5 $\mu$M did not affect the enzymatic activity of LPL.

Figure 5:
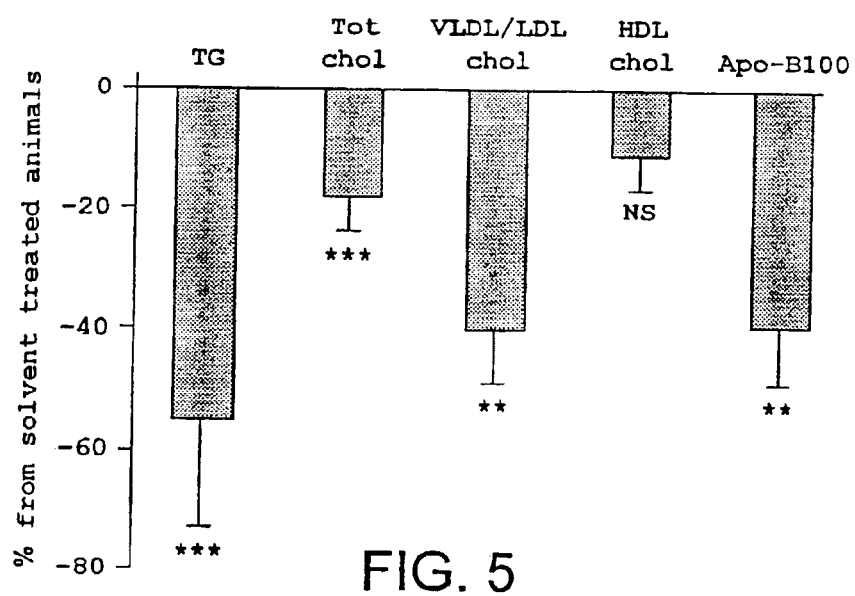
FIG. 5 shows the decrease in various lipid levels resulting from administration of test TGH inhibitor to normal fed hamsters.

5. Hypolipidemic Activity of the TGH Inhibitors in Hamster:

As shown in FIG. 5, the oral administration of 4,4,4-trifluoro-2-[2-(3-methylphenyl)hydrazono]-1-(2-thienyl) butane-1,3-dione resulted in significant reduction in the plasma TG concentration (−55% from the solvent treated animals) as well as in the VLDL/LDL cholesterol (40% from the solvent treated animals) while HDL cholesterol level was not significantly affected. ApoB100 was also reduced to the same extent as Apo-B100 containing particles (−39% decrease compared to control animals).

Tablet Compositions

The following compositions A and B can be prepared by wet granulation of ingredients (a) to (c) and (a) to (d) with a solution of povidone, followed by addition of the magnesium stearate and compression.

Composition A

|     |                        | mg/tablet | mg/tablet |
| --- | ---------------------- | --------- | --------- |
| (a) | Active ingredient      | 250       | 250       |
| (b) | Lactose B.P.           | 210       | 26        |
| (c) | Sodium Starch Glycollate | 20      | 12        |
| (d) | Povidone B.P.          | 15        | 9         |
| (e) | Magnesium Stearate     | 5         | 3         |
|     |                        | 500       | 300       |

Composition B

|     |                        | mg/tablet | mg/tablet |
| --- | ---------------------- | --------- | --------- |
| (a) | Active ingredient      | 250       | 250       |
| (b) | Lactose 150            | 150       | —         |
| (c) | Avicel PH 101          | 60        | 26        |
| (d) | Sodium Starch Glycollate | 20      | 12        |
| (e) | Povidone B.P.          | 15        | 9         |
| (f) | Magnesium Stearate     | 5         | 3         |
|     |                        | 500       | 300       |

Composition C

|                     | mg/tablet |
| ------------------- | --------- |
| Active ingredient   | 100       |
| Lactose             | 200       |
| Starch              | 50        |
| Povidone            | 5         |
| Magnesium Stearate  | 4         |
|                     | 359       |

The following compositions D and E can be prepared by direct compression of the admixed ingredients. The lactose used in composition E is of the direct compression type.

Composition D

|                          | mg/tablet |
| ------------------------ | --------- |
| Active ingredient        | 250       |
| Magnesium Stearate       | 4         |
| Pregelatinised Starch NF15 | 146    |
|                          | 400       |

Composition E

|                    | mg/tablet |
| ------------------ | --------- |
| Active ingredient  | 250       |
| Magnesium Stearate | 5         |
| Lactose            | 145       |
| Avicel             | 100       |
|                    | 500       |

Composition F (Controlled release composition)

|     |                                                  | mg/tablet |
| --- | ------------------------------------------------ | --------- |
| (a) | Active ingredient                                | 500       |
| (b) | Hydroxypropylmethylcellulose (Methocel K4M Premium) | 112   |
| (c) | Lactose B.P.                                     | 53        |
| (d) | Povidone B.P.C.                                  | 28        |
| (e) | Magnesium Stearate                               | 7         |
|     |                                                  | 700       |

The composition can be prepared by wet granulation of ingredients (a) to (c) with a solution of povidone, followed by addition of the magnesium stearate and compression.

Composition G (Enteric-Coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-Coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

Composition B

|     |                          | mg/capsule |
| --- | ------------------------ | ---------- |
| (a) | Active ingredient        | 250        |
| (b) | Lactose B.P.             | 143        |
| (c) | Sodium Starch Glycollate | 25         |
| (d) | Magnesium Stearate       | 2          |
|     |                          | 420        |

Composition C

|     |                   | mg/capsule |
| --- | ----------------- | ---------- |
| (a) | Active ingredient | 250        |
| (b) | Macrogol 4000 BP  | 350        |
|     |                   | 600        |

Capsules can be prepared by melting the Macrogol 4000 BP, dispersing the active ingredient in the melt and filling two-part hard gelatin capsules therewith.

Composition D

|  | mg/capsule |
|---|---|
| Active ingredient | 250 |
| Lecithin | 100 |
| Arachis Oil | 100 |
|  | 450 |

Capsules can be prepared by dispersing the active ingredient in the lecithin and arachis oil and filling soft, elastic gelatin capsules with the dispersion.

Composition E (Controlled release capsule)

| | Composition E (Controlled release capsule) | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
| | | 513 |

The controlled release capsule composition can be prepared by extruding mixed ingredients (a) to (c) using an extruder, then spheronising and drying the extrudate. The dried pellets are coated with a release controlling membrane (d) and filled into two-part, hard gelatin capsules.

| | Composition F (Enteric capsule) | mg/capsule |
|---|---|---|
| (a) | Active ingredient | 250 |
| (b) | Microcrystalline Cellulose | 125 |
| (c) | Lactose BP | 125 |
| (d) | Cellulose Acetate Phthalate | 50 |
| (e) | Diethyl Phthalate | 5 |
| | | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-Coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(iii) Intravenous Injection Composition

| Active ingredient | 0.200 g |
|---|---|
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml glass vials (Type 1) which are sealed with sterile closures and overseals.

(iv) Intramuscular Injection Composition

| Active ingredient | 0.20 g |
|---|---|
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

(v) Syrup Composition

| Active ingredient | 0.25 g |
|---|---|
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

(vi) Suppository Composition

|  | mg/suppository |
|---|---|
| Active ingredient | 250 |
| Hard Fat, BP (witepsol H15 - Dynamit NoBel) | 1770 |
|  | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

(vii) Pessary Composition

|  | mg/pessary |
| --- | --- |
| Active ingredient (63 lm) | 250 |
| Anhydrous Dextrose | 380 |
| Potato Starch | 363 |
| Magnesium Stearate | 7 |
|  | 1000 |

The above ingredients are mixed directly and pessaries prepared by compression of the resulting mixture.

(viii) Transdermal Composition

| Active ingredient | 200 mg |
| --- | --- |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

REFERENCES

1] LaRosa J C, Hunninghake D, Grundy S M, Wilson P W, Clarkson T B, Hay J W.
The cholesterol facts. A summary of the evidence relating dietary habits, serum cholesterol, and coronary heart disease. A joint statement by the American Heart Association and the National Heart, Lung, and Blood Institute. Circulation 1990;81:1721–1733.

2] Neaton J D, Wentworth D F. Serum cholesterol, blood pressure, cigarette smoking and death from coronary heart disease. Overall findings and differences by age for 316, 099 white men. Arch Intern Med 1992;152:56–63.

3] Blankenhorn D H, Azen S P, Kramsch D M Mack W J. Cashin-Hemphill L. Hodis H N. DeBoer L W. Mahrer P R. Masteller M J. Vailas Li. et al. Coronary changes with lovastatin therapy: the monitored atherosclerosis regression study (MARS). Ann Intern Med 1993;119:969–976.

4] Effect of Simvastatin on coronary atheroma: the Multi-centre Anti-Atheroma Study (MAAS). Lancet 1994;344:633–638.

5] Blankenhorn D H, Nessim A, Johnson R L, Sanmarco M E, Azen S P, Cashin-HemphillL. Beneficial effects of combined colestipolniacin therapy on coronary atherosclerosis and coronary venous bypass grafts. J Am Med Assoc 1987;257:3233–3240.

6] Howard B V. Lipoprotein metabolism in diabetes mellitus. J Lipid Res 1987;28:613628

7] Laws A. Free fatty acids, insulin resistance and lipoprotein metabolism. Curr. Opin. Lipidol 1996;7:172–177.

8] Gibbons G F. Bartlett S M. Sparks C E. Sparks J D. Extracellular fatty acids are not utilized directly for the synthesis of very-low-density lipoprotein in primary cultures of rat hepatocytes. Biochemical Journal 1992; 287:749–753.

9] Francone O L. Kalopissis A D. Griffaton G. Contribution of cytoplasmic storage triacylglycerol to VLDL-triacylglycerol in isolated rat hepatocytes. Biochimica et Biophysica Acta. 1989; 1002:28–36.

10] Gibbons G F. Wiggins D. Intracellular triacylglycerol lipase: its role in the assembly of hepatic very-low-density lipoprotein (VLDL). Advances in Enzyme Regulation., 1995; 35:179–198

11] Yang L Y. Kuksis A. Myher J J. Steiner G. Contribution of de novo fatty acid synthesis to very low density lipoprotein triacylglycerols: evidence from mass isotopomer distribution analysis of fatty acids synthesized from [2H6]ethanol. Journal of Lipid Research. 1996; 37:262–74.

12] Wiggins D. Gibbons G F. The lipolysis/esterification cycle of hepatic triacyiglycerol. Its role in the secretion of very-low-density lipoprotein and its response to hormones and sulphonylureas. Biochemical Journal. 1992; 284:457–62.

13] Lehner R. Verger R. Purification and characterization of a porcine liver microsomal triacylglycerol hydrolase. Biochemistry. 1997; 36:1861–1868.

14] Lehner R. Cui Z. Vance D E. Subcellullar localization, developmental expression and characterization of a liver triacylglycerol hydrolase. Biochemical Journal. 1999;338:761–768.

15] Lehner R and Vance D E. Cloning and expression of a cDNA encoding a hepatic microsomal lipase that mobilizes stored triacyiglycerol. Biochemical Journal. (October) 1999;343:1–10R 16] Buchwald H. Vargo R L. Matts J P, Long J M, Fitch L L, Campbell G S, Pearce M B, Yellin A E, Edmiston W A, Smink R D Jr et al. Effect of partial ilial bypass on mortality and morbidity from coronary artery disease in patients with hypercholesterolemia—Report of the Program on surgical Control of the Hyperlipidemia (POSCH). New Engi J. Med. 1990;323:946.

17] Becker A. Böttcher A. Lackner K J. Fehringer P. Notka F. Aslanidis C. Schmitz G. Purification, cloning, and purification of a Human enzyme with Acyl coenzyme A cholesterol acyltransferase activity, which is identical to liver carboxylesterase. Arterioscler Thromb. 1994;14:1346–1355.

What is claimed is:

1. A method for identifying a compound which decreases, in a mammal, circulating levels of a molecule selected from:

i) triglycerides;

ii) very-low-density lipoprotein (VLDL)/low density lipoprotein (LDL)-cholesterol; and iii) Apo B-100;

comprising the step of determining whether a test compound specifically inhibits triacylglycerol hydrolase (TGH) activity, wherein said test compound specifically inhibits TGH activity, said compound decreases circulating levels of said molecule in a mammal without significantly decreasing HDL level.

2. The method according to claim 1 where the TGH is human TGH.

3. A The method according to claim 1 whereby the difference in enzymatic activity of TGH on a fluorogenic control substrate in the presence of a test compound is compared to the enzymatic activity of TGH which occurs in the absence of said test compound.

* * * * *